(12) United States Patent
Koehler et al.

(10) Patent No.: US 6,747,176 B2
(45) Date of Patent: Jun. 8, 2004

(54) PREPARATION OF 2-CHLORO-1,1,1-TRIALKOXYETHANE

(75) Inventors: Guenther Koehler, Marl (DE); Karl-Heinz Bruehl, Velen (DE); Johannes Ruwwe, Niederkassel (DE); Manfred Neumann, Marl (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/457,570

(22) Filed: Jun. 10, 2003

(65) Prior Publication Data

US 2003/0229255 A1 Dec. 11, 2003

(30) Foreign Application Priority Data

Jun. 10, 2002 (DE) .......................... 102 25 750

(51) Int. Cl.$^7$ .............................. C07C 43/30
(52) U.S. Cl. ................. 568/595; 568/591; 568/592; 568/600; 568/604
(58) Field of Search ................. 568/595, 591, 568/592, 600, 604

(56) References Cited

U.S. PATENT DOCUMENTS

| 4,723,010 A | 2/1988 | Mylari et al. ............ 546/114 |
| 4,748,280 A | 5/1988 | Mylari et al. ............ 568/595 |
| 5,831,089 A | 11/1998 | Huber .................... 540/562 |
| 6,281,392 B1 * | 8/2001 | Burkart et al. ........... 568/595 |

FOREIGN PATENT DOCUMENTS

| EP | 0 222 576 | 5/1987 |
| WO | WO 01/96315 | 12/2001 |

OTHER PUBLICATIONS

Moos et al., Codeine Analogues. Synthesis of Spiro [benzofuran–3(2H),4'–piperidines] and Octahydro–1–H–benzofuro[3,2–e]isoquinolines, J. Org. Chem., Dec. 1981, vol. 46, No. 25, pp. 5064–5074.*

Elworthy et al., On the Utility of alpha.Heteroatom Substituted Orthoesters in the Johnson Claisen Rearrangement, Tetrahedron Letters, May 1994, vol. 35, Nol 28, pp. 4951–4954.*

K. Kamata, et al., Heterocycles, vol. 51, No. 2, pp. 373–378, XP–002176381, "Synthesis of Optically Active 2–Chloromethyl–2–Oxazolines by the Ortho–Ester Condensation Method Using Triethyl Orthochloroacetate", 1999.

C. J. Cowden, et al., Tetrahedron Letters, vol. 41, pp. 8661–8664, "A New Synthesis of 1,2,4–Triazolon–5–Ones: Application to the Convergent Synthesis of an NK$_1$ Antagonist", 2000.

Y. Takemoto, J. Org. Chem., vol. 66, pp. 6116–5123, "Stereospecific 1,3–Migration of an Fe(CO)$_3$ Group on Acyclic Conjugated Polyenes:Application to Remote and Iterative Asymmetric Induction", 2001.

S. Sanchez, et al., Tetrahedron Letters, vol. 41, pp. 7447–7452, "A Comprehensive Glycosylation System for the Elaboration of Oligoarabinofuranosides", 2000.

B. L. Mylari, et al., Synthetic Communications, vol. 19, No. 16, pp. 2921–2924, "2–Chloro–1, 1, 1–Triethoxyethane and its use in a Versatile Synthesis of Substituted, 2–Chloromethyl Heterocycles Including Benzothiazole and Benzoxazole", 1989.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

2-Chloro-1,1,1-trialkoxyethane of formula (II):

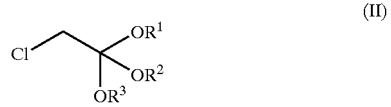

wherein $R^1$ to $R^3$, which may be the same or different, are alkyl, or any two of the alkyl groups taken together form a cyclic group, is prepared by reacting 1,1,1-trialkoxyethane with gaseous or liquid chlorine in the presence of alcohol solvent in an amount ranging from 0.1% to 20 wt %, based on the amount of 1,1,1-trialkoxyethane reactant.

14 Claims, No Drawings

PREPARATION OF 2-CHLORO-1,1,1-TRIALKOXYETHANE

BACKGROUND OF THE INVENTION

1. Field of the Invention

The present invention relates to a process for preparing 2-chloro-1,1,1-trialkoxyethane (II) (monochlorinated orthoacetic ester) by reacting 1,1,1-trialkoxyethane (I) (orthoacetic ester) with chlorine, preferably in the presence of alcohols and catalytic amounts of a base:

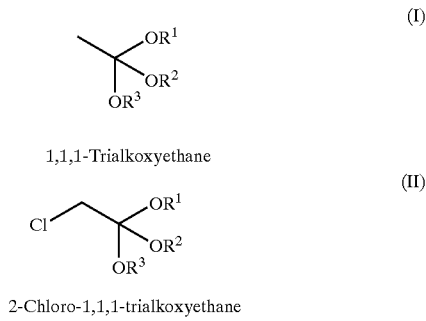

1,1,1-Trialkoxyethane

2-Chloro-1,1,1-trialkoxyethane

2. Description of the Background

2-Chloro-1,1,1-trialkoxyethane compounds (chlorinated orthoacetic esters) are important raw materials and building blocks for active ingredients in the pharmaceutical and agrochemical industries. Overall, they are suitable in a versatile manner for constructing heterocyclic compounds. For instance, the reaction of chlorinated orthoacetic esters with semicarbazide hydrochloride to give substituted triazolones is described in Tetrahedron Letters, 41(44), 8661–8664; 2000 and in the patent application WO01/96315. Moreover, chlorinated orthoacetic esters are described in the Journal of Organic Chemistry, 66 (18) 6116–6123; 2001 and in Tetrahedron Letters 41 (39), 7447–7452; 2000, as building blocks for substituted cyclic ketals and lactones.

In U.S. Pat. No. 5,831,089, 2-chloro-1,1,1-trialkoxyethane serves as a building block with an amine as a reactant for preparing substituted amido esters.

Synth. Commun. 19 (16), 2921–2924 describes both the use of 2-chloro-1,1,1-triethoxyethane as a versatile building block for preparing benzothiazoles and benzoxazoles and also the preparation by reaction of triethyl orthoacetate with N-chlorosuccinimide.

As taught in the prior art, 2-chloro-1,1,1-orthoesters are prepared by reacting orthoesters with chlorosuccinimide, in many cases in large amounts of chlorinated hydrocarbons. For instance, European patent application EP 0 222 576 describes the synthesis of 2-chloro-1,1,1-triethoxyethane starting from 1,1,1-triethoxyethane with N-chlorosuccinimide in the presence of carbon tetrachloride as solvent. Further prior art examples can be found in EP 0 222 576 and in U.S. Pat. No. 4,748,280 (7.31.1987), which disclose the synthesis of 2-chloro-1,1,1-($C_1$–$C_4$)-alkoxyethane by reacting 1,1,1-($C_1$–$C_4$)-alkoxyethane with N-chlorosuccinimide in the presence of chlorinated hydrocarbons as the solvent. The last-cited patent suggests a further synthetic route of reacting the same reactant with chlorine in the presence of stoichiometric amounts of pyridine as base, using chlorinated hydrocarbon as a cosolvent. Common to all these processes is that the space-time yield of product is uneconomical from the aspect of technical and industrial application, and the processes can only be carried out at very high cost and inconvenience. In addition, halohydrocarbons are frequently used as solvents. However, such halohydrocarbon solvents are used with reluctance in the chemical industry from the point of view of environmental protection. A further economic drawback of the conventional processes using N-chlorosuccinimide is the very high price of this raw material. Furthermore, the use of N-chlorosuccinimide results, after completion of the synthesis, in succinimide as waste material which, as a solid, has to be removed at great cost and inconvenience from the reaction mixture by a solids work-up (filtering, decanting or centrifuging). This also makes industrial application very disadvantageous. In addition to the drawbacks already mentioned, it is common to all the prior art processes that a relatively high proportion of 2,2-dichloro-1,1,1-trialkoxyethane occurs which can only be removed from monochloro-1,1,1-trialkoxyethane in a subsequent work-up of the reaction mixture at very high costs of distillation. Moreover, for monochloro-1,1,1-trialkoxyethanes that are used in the pharmaceutical sector, it is desirable that very pure products be obtained that contain very low amounts of dichlorinated by-products.

SUMMARY OF THE INVENTION

Accordingly, one object of the present invention is to provide an improved method of preparing 2-chloro-1,1,1-trialkoxyethane that minimizes production costs and results in a product of high purity.

Briefly, this object and other objects of the present invention as hereinafter will become more readily apparent can be attained by a process of preparing 2-chloro-1,1,1-trialkoxyethane in high purity by reacting 1,1,1-trialkoxyethane with gaseous or liquid chlorine in the presence of an alcohol and preferably of a catalytic amount of base.

DETAILED DESCRIPTION OF THE PREFERRED EMBODIMENTS

In formulas (I) and (II) above, which respectively represent reactant and product, $R_1$, $R_2$ and $R_3$ are the same or different and each is an alkyl radical containing from 1 to 8, preferably from 1 to 6, more preferably from 1 to 4, carbon atoms. However, two or three of the radicals they may also be joined together to form a cyclic alkylene group. Suitable alkyl groups include methyl, propyl, isopropyl, n-butyl, isobutyl and sec-butyl groups. The cyclic alkylene group preferably contains 2 to 3 carbon atoms. The alcohol may be linear or branched or may be an aromatic group.

The total number of carbon atoms in the alcohol solvent ranges from 1 to 10. Suitable examples of alcohols include methanol, ethanol, the isomeric propanols, the isomeric butanols and benzyl alcohol.

The reaction of the invention is performed at a temperature from –20° C. to +100° C., and preferably at atmospheric pressure. However, slightly increased pressures of up to about 10 bar, preferably 5 bar (absolute) may also be employed. Relatively small amounts of solvent are used, and preference is given to low-boiling low molecular weight alcohols which can be removed easily by distillation. The amount of alcohol solvent in the reaction generally ranges from 0.1 to 20%, preferably from 5 to 20%, based on the 1,1,1-trialkoxyethane used. The reaction may also be conducted without the presence of an alcohol, which has the advantage that a step of distillation in the work-up to obtain a pure reaction product is not required thus simplifying the process. When an alcohol solvent is employed in the reaction, a relatively large proportion of by-product materials is to be expected. In particular, with respect to the degradation of the orthoacetates, ethyl acetate is obtained as a by-product.

In the chlorination reaction, gaseous or liquid chlorine is metered into the reactor or into the orthoacetate or the initially charged orthoacetate/alcohol mixture. Because the chlorination is strongly exothermic ($\Delta H$ approx. $-100$ kJ/mol), chlorine is preferably introduced into the reaction medium in batches or slowly at a low metering rate, so that the internal temperature does not rise to such an extent that selectivity is adversely affected. It has been found that a tolerably narrow by-product spectrum occurs within a temperature range ranging from $-20°$ C. to a maximum of $100°$ C.

The use of catalytic amounts of a base when initiating the chlorination reaction surprisingly proves to be advantageous. Suitable bases include small amounts of alkali metal hydroxide or alkali metal alkoxide, in particular sodium alkoxide or potassium alkoxide, for example sodium methoxide, sodium ethoxide, sodium isopropoxide, potassium methoxide, potassium ethoxide, potassium tert-butoxide or potassium sec-butoxide. The bases may be used as pure substances, for example, as a solid in powder or granule form, or else in the form of an alcoholic solution. According to the invention, the amount of pure base when used should range from 0.1 to 10%, preferably from 0.2 to 1% (based on trialkoxyethane used).

From economic considerations, the content of alcohol which may be used to dissolve the base should preferably not be greater than 20%, based on the orthoester used.

The process of the invention may be conducted batchwise or continuously. In the case of a continuous process operation, only as much of the reaction mixture is withdrawn as is added in reactants, so that the fill level in the reactor remains constant. At the start of the reaction, it is advisable to bring the conversion to a very high level. The required reaction or residence times, depending on the heat of reaction which can be removed, are in the range of 2–10 hours. The times are substantially determined by the available cooling performance and the reactor design. However, all process variants mentioned provide a better conversion within shorter reaction times at very high selectivity compared to conventional prior art processes. Depending on the orthoester or the proportion of alcohol used, the dichlorinated proportion of the orthoester is usually well below two percent, so that distillative purification of the product leads to a highly pure monochloroorthoacetate with economically tolerable distillation losses.

In contrast to conventional processes, no solids are obtained, except when using small amounts of alkali metal alkoxide, are obtained in the form of chlorides. However, such small amounts of solid of approx. 0.1 to 1% can be easily removed mechanically, for example, using simple filter candles, before the reaction mixture is worked-up by distillation, which avoids solid deposits in the distillation plant.

Having generally described this invention, a further understanding can be obtained by reference to certain specific examples which are provided herein for purposes of illustration only and are not intended to be limiting unless otherwise specified.

EXAMPLE 1

A 500 ml flask equipped with a stirrer and gas inlet tube was initially charged at $10°$ C. with a mixture of 240 g (2 mol) of 1,1,1-trimethoxyethane and 1% of $NaOCH_3$ (30%). Within 4 hours, 110 g of chlorine were introduced into the flask in gaseous form, and the internal temperature of the flask did not rise above $15°$ C. Once the entire amount of chlorine had been introduced into the flask, the mixture was worked-up by distillation. Using a distillation apparatus having approx. 5 theoretical plates, low boilers such as methanol and methyl acetate were removed in the first stages of distillation at a reflux ratio of 5:1. In the main fraction, 234 g of 2-chloro-1,1,1-trimethoxyethane in a purity of >99.0% were obtained at a reflux ratio of 2:1. This amount of product corresponds to a yield of approx. 76%.

EXAMPLE 2

A 1000 ml flask equipped with a stirrer and gas inlet tube was initially charged at $10°$ C. with a mixture of 480 g (4 mol) of 1,1,1-trimethoxyethane and 48 g (10% by weight) of methanol. Within 4 hours, 220 g (3.14 mol) of chlorine were introduced into the flask in gaseous form, and the internal temperature of the flask did not rise above $15°$ C. Once the entire amount of chlorine had been introduced into the flask, the mixture was worked-up by distillation. A distillation apparatus having approx. 5 theoretical plates was used to remove low boilers such as ethanol and ethyl acetate in the first stages of distillation at a reflux ratio of 5:1. In the main fraction, 425 g of 2-chloro-1,1,1-triethoxyethane in a purity of >99.0% were obtained at a reflux ratio of 2:1. This amount of product corresponds to a yield of approx. 69%.

EXAMPLE 3

A 1000 ml flask equipped with a stirrer and gas inlet tube was initially charged at $10°$ C. with 480 g (4 mol) of 1,1,1-trimethoxyethane. Within 4 hours, 220 g (3.14 mol) of chlorine were introduced into the flask in gaseous form, and the internal temperature of the flask did not rise above $15°$ C. Once the entire amount of chlorine had been introduced into the flask, the mixture was worked-up by distillation. A distillation apparatus having approx. 5 theoretical plates was used to remove low boilers such as methanol and methyl acetate in the first stages at a reflux ratio of 5:1. In the main fraction, 413 g of 2-chloro-1,1,1-trimethoxyethane in a purity of >99.0% were obtained at a reflux ratio of 2:1. This amount of product corresponds to a yield of approx. 67%.

EXAMPLE 4

A 1000 ml flask equipped with a stirrer and gas inlet tube was initially charged at $10°$ C. with a mixture of 648 g (4 mol) of 1,1,1-triethoxyethane and 70 g (approx. 11% by weight) of ethanol. Within 4 hours, 260 g (3.70 mol) of chlorine were introduced into the flask in gaseous form, and the internal temperature of the flask did not rise above $15°$ C. Once the entire amount of chlorine had been introduced into the flask, the mixture was worked-up by distillation. A distillation apparatus having approx. 5 theoretical plates was used to remove low boilers such as methanol and methyl acetate in the first stages at a reflux ratio of 5:1. In the main fraction, 520 g of 2-chloro-1,1,1 trimethoxyethane in a purity of >99.0% were obtained at a reflux ratio of 2:1. This amount of product corresponds to a yield of approx. 67%.

German patent Number 10225750.7 filed Jun. 10, 2002 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A process for preparing 2-chloro-1,1,1-trialkoxyethane of formula (II):

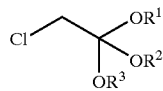

wherein $R^1$ to $R^3$, which may be the same or different, are alkyl, or any two of the alkyl groups taken together form a cyclic group, comprising:
reacting 1,1,1-trialkoxyethane with gaseous or liquid chlorine in the presence of alcohol solvent in an amount ranging from 0.1% to 20 wt %, based on the amount of 1,1,1-trialkoxyethane reactant.

2. The process as claimed in claim 1, wherein the alkyl groups have from 1 to 8 carbon atoms.

3. The process as claimed in claim 1, wherein the alkyl groups have from 1 to 4 carbon atoms.

4. The process as claimed in claim 2, wherein the alkyl groups are selected from the group consisting of methyl, ethyl, propyl, isopropyl, n-butyl, isobutyl and sec-butyl group, or, when two groups are taken together, form a cyclic group that contains 2–3 carbon atoms.

5. The process as claimed in claim 1, wherein the alcohol solvent has from 1 to 10 carbon atoms.

6. The process as claimed in claim 5, wherein the alcohol solvent contains a straight-chain or branched carbon chain or contains an aromatic group.

7. The process as claimed in claim 1, wherein the amount of alcohol, based on the 1,1,1-trialkoxyethane used, ranges from 5 to 20 wt %.

8. The process as claimed in claim 1, wherein the reaction medium further comprises a base.

9. The process as claimed in claim 8, wherein the base is an alkali metal alkoxide.

10. The process as claimed in claim 9, wherein the base is sodium methoxide, sodium ethoxide, sodium isopropoxide, potassium methoxide, potassium ethoxide, potassium t-butoxide or potassium sec-butoxide.

11. The process as claimed in claim 8, wherein the amount of base ranges from 0.1 to 10 wt %.

12. The process as claimed in claim 1, wherein the temperature of the reaction ranges from −20° C. to 100° C.

13. The process as claimed in claim 1, wherein the reaction is conducted at a pressure ranging from 1 to 5 bar absolute.

14. The process as claimed in claim 1, wherein the reaction is conducted in a batchwise manner or continuously.

* * * * *